US012697336B2

(12) United States Patent
Joshi

(10) Patent No.: US 12,697,336 B2
(45) Date of Patent: Aug. 4, 2026

(54) RUC-4 FORMULATIONS

(71) Applicant: CeleCor Therapeutics, Inc., Del Mar, CA (US)

(72) Inventor: Yatindra Joshi, North Wales, PA (US)

(73) Assignee: CeleCor Therapeutics, Inc., Del Mar, CA (US)

( * ) Notice: Subject to any disclaimer, the term of this patent is extended or adjusted under 35 U.S.C. 154(b) by 423 days.

(21) Appl. No.: 18/277,363

(22) PCT Filed: Feb. 16, 2022

(86) PCT No.: PCT/US2022/016564
§ 371 (c)(1),
(2) Date: Aug. 15, 2023

(87) PCT Pub. No.: WO2022/177962
PCT Pub. Date: Aug. 25, 2022

(65) Prior Publication Data

US 2025/0281490 A1 Sep. 11, 2025

Related U.S. Application Data

(60) Provisional application No. 63/150,168, filed on Feb. 17, 2021.

(51) Int. Cl.

| | |
|---|---|
| ***A61K 31/519*** | (2006.01) |
| ***A61K 9/08*** | (2006.01) |
| ***A61K 9/19*** | (2006.01) |
| ***A61K 47/02*** | (2006.01) |
| ***A61K 47/10*** | (2017.01) |
| ***A61K 47/12*** | (2006.01) |

(52) U.S. Cl.
CPC .............. *A61K 31/519* (2013.01); *A61K 9/08* (2013.01); *A61K 9/19* (2013.01); *A61K 47/02* (2013.01); *A61K 47/10* (2013.01); *A61K 47/12* (2013.01)

(58) Field of Classification Search
CPC ............................ A61K 31/519; C07D 513/04
See application file for complete search history.

(56) References Cited

U.S. PATENT DOCUMENTS

| | | | |
|---|---|---|---|
| 4,265,898 | A | 5/1981 | Horstmann et al. |
| 6,221,335 | B1 | 4/2001 | Foster |
| 6,603,008 | B1 | 8/2003 | Ando et al. |
| 7,517,990 | B2 | 4/2009 | Ito et al. |
| 9,303,044 | B2 | 4/2016 | Coller et al. |
| 9,532,989 | B2 | 1/2017 | Coller et al. |
| 11,684,622 | B2 | 6/2023 | Joshi |
| 2007/0082929 | A1 | 4/2007 | Gant et al. |
| 2007/0197695 | A1 | 8/2007 | Potyen et al. |
| 2015/0050325 | A1 | 2/2015 | Coller et al. |
| 2021/0361658 | A1 | 11/2021 | Joshi |
| 2023/0364094 | A1 | 11/2023 | Joshi |
| 2025/0268902 | A1 | 8/2025 | Joshi |

FOREIGN PATENT DOCUMENTS

| | | | |
|---|---|---|---|
| CN | 104936598 | A | 9/2015 |
| WO | WO 2009/024615 | A1 | 2/2009 |
| WO | WO 2019/246085 | A1 | 12/2019 |

OTHER PUBLICATIONS

Extended European Search Report for EP 19823013.8, mailed Feb. 25, 2022.
International Search Report and Written Opinion for Application No. PCT/US2019/037713, mailed Aug. 23, 2019.
International Preliminary Report on Patentability for Application No. PCT/US2019/037713, mailed Dec. 30, 2020.
International Search Report and Written Opinion for Application No. PCT/US2022/016564, mailed May 4, 2022.
International Preliminary Report on Patentability for Application No. PCT/US2022/016564, mailed Aug. 31, 2023.
International Search Report and Written Opinion for Application No. PCT/US2022/016571, mailed May 3, 2022.
International Preliminary Report on Patentability for Application No. PCT/US2022/016571, mailed Aug. 31, 2023.
Baba et al., Studies on drug metabolism by use of isotopes. 23. Metabolic study of 1-butyryl-4-cinnamylpiperazine in the rat during development of tolerance by using two kinds of deuterium-labeled forms. J Med Chem. Jun. 1978;21(6):525-9. doi: 10.1021/jm00204a005.
Declaration under 37 C.F.R. § 1.32 of Vinita Uttamsingh, dated Feb. 1, 2012. 3 pages. Filed in U.S. Appl. No. 12/102,164, filed Apr. 14, 2008.
Foster, Deuterium isotope effects in the metabolism of drugs and xenobiotics: implications for drug design. Advances in Drug Research. 1985; 14: 1-40.
Harbeson et al., Chapter 24: Deuterium in Drug Discovery and Development. Annual Reports in Medicinal Chemistry. Concert Pharmaceuticals, Inc. Lexington, MA. 2011;46:403-417.
Jiang et al., A novel class of ion displacement ligands as antagonists of the αIIbβ3 receptor that limit conformational reorganization of the receptor. Bioorg Med Chem Lett. Feb. 15, 2014;24(4):1148-53. doi: 10.1016/j.bmcl.2013.12.122. Epub Jan. 8, 2014.
Kereiakes et al., First Human Use of RUC-4: A Nonactivating Second-Generation Small-Molecule Platelet Glycoprotein IIb/IIIa (Integrin αIIbβ3) Inhibitor Designed for Subcutaneous Point-of-Care Treatment of ST-Segment-Elevation Myocardial Infarction. J Am Heart Assoc. Sep. 2020;9(17):e016552. doi: 10.1161/JAHA.120.016552. Epub Aug. 26, 2020.
Li et al., RUC-4: a novel αIIbβ3 antagonist for prehospital therapy of myocardial infarction. Arterioscler Thromb Vasc Biol. Oct. 2014;34(10):2321-9. doi: 10.1161/ATVBAHA.114.303724. Epub Aug. 21, 2014.

(Continued)

*Primary Examiner* — Kamal A Saeed
(74) *Attorney, Agent, or Firm* — Wolf, Greenfield & Sacks, P.C.

(57) ABSTRACT

The present disclosure relates to solid and liquid formulations of RUC-4 that are stable under a range of storage conditions.

23 Claims, 17 Drawing Sheets

(56) References Cited

OTHER PUBLICATIONS

Liu, Deuterated Drugs Progress. Chemical Engineering Design Communications. Apr. 2016; 42(4): 199 and 238.
No Author Listed, Pubchem SID: 384568713. Deposit Date: Jun. 21, 2019. 7 pages.
Savonitto et al., Antithrombotic therapy before, during and after emergency angioplasty for ST elevation myocardial infarction. Eur Heart J Acute Cardiovasc Care. Mar. 2017;6(2):173-190. doi: 10.1177/2048872615590148. Epub Sep. 22, 2016.
Shao et al., Derivatives of tramadol for increased duration of effect. Bioorg Med Chem Lett. Feb. 2006;16(3):691-4. doi: 10.1016/j.bmcl.2005.10.024. Epub Oct. 27, 2005.
Strickley, Solubilizing excipients in oral and injectable formulations. Pharm Res. Feb. 2004;21(2):201-30. doi: 10.1023/b:pham.0000016235.32639.23.
Wolen, The application of stable isotopes to studies of drug bioavailability and bioequivalence. J Clin Pharmacol. Jul.-Aug. 1986;26(6):419-24. doi: 10.1002/j.1552-4604.1986.tb03551.x.
Xu et al., High-sensitive cardiac troponin T. J Geriatr Cardiol. Mar. 2013;10(1):102-9. doi: 10.3969/j.issn.1671-5411.2013.01.015.
Extended European Search Report for Application No. 22756816.9, mailed Dec. 18, 2024.
Extended European Search Report for Application No. 22756821.9, mailed Dec. 17, 2024.
No Author Listed, Clinicaltrials ID No. NCT04284995. A Phase 2 Open Label Study to Assess the PK/PD Properties of RUC-4 in Patients With a ST-elevation Myocardial Infarction (CEL-02). Version 8. Submitted Sep. 25, 2020. Retrieved from the Internet: https://clinicaltrials.gov/study/NCT04284995.
No Author Listed, Clinicaltrials ID No. NCT03844191. A Randomized Phase 1 Dose-Escalation Study of Subcutaneously(SC) Administered RUC-4. Version 6. Submitted Feb. 18, 2020. Retrieved from the Internet: https://clinicaltrials.gov/study/NCT03844191.
Tavenier et al., Bridging the gap: Current and future insights for improving suboptimal platelet inhibition in STEMI. Int J Cardiol. Apr. 1, 2021:328:40-45. doi: 10.1016/j.ijcard.2020.11.042. Epub Nov. 23, 2020.
Van'T Hof et al., Zalunfiban at First Medical Contact for ST-Elevation Myocardial Infarction. NEJM Evid. Jan. 2026;5(1):EVIDoa2500268. doi: 10.1056/EVIDoa2500268. Epub Nov. 10, 2025.

| | SR | SS | ST | SY | SZ | SAB |
|---|---|---|---|---|---|---|
| RUC4 concentration | 22 mg/mL | 22 mg/mL | 10 mg/mL | 22 mg/mL | 10 mg/mL | 18 mg/mL |
| Initial Solution pH | 5.99 | 4.98 | 4.98 | 5.06 | 4.97 | 4.98 |
| Glycerin (mg/mL) | -- | -- | -- | 9 | 18 | 14 |
| NaCl (mg/mL) | 4.4 | 4.1 | 6.17 | -- | -- | -- |
| Acid | AcOH-HCl | AcOH-HCl | AcOH-HCl | AcOH-HCl | AcOH-HCl | AcOH-HCl |

| | SR | SS | ST | SY | SZ | SAB |
|---|---|---|---|---|---|---|
| RUC4 concentration | 22 mg/mL | 22 mg/mL | 10 mg/mL | 22 mg/mL | 10 mg/mL | 18 mg/mL |
| Initial Solution pH | 5.99 | 4.98 | 4.98 | 5.06 | 4.97 | 4.99 |
| Glycerin (mg/mL) | -- | -- | -- | 9 | 18 | 14 |
| NaCl (mg/mL) | 4.4 | 4.1 | 6.17 | -- | -- | -- |
| Acid | AcOH-HCl | AcOH-HCl | AcOH-HCl | AcOH-HCl | AcOH-HCl | AcOH-HCl |

| | SR | SS | ST | SY | SZ | SAB |
|---|---|---|---|---|---|---|
| RUC4 concentration | 22 mg/mL | 22 mg/mL | 10 mg/mL | 22 mg/mL | 10 mg/mL | 18 mg/mL |
| Initial Solution pH | 5.99 | 4.98 | 4.98 | 5.06 | 4.97 | 4.99 |
| Glycerin (mg/mL) | -- | -- | -- | 9 | 18 | 14 |
| NaCl (mg/mL) | 4.4 | 4.1 | 6.17 | -- | -- | -- |
| Acid | AcOH-HCl | AcOH-HCl | AcOH-HCl | AcOH-HCl | AcOH-HCl | AcOH-HCl |

| | SA | SB | SC | SD | SE | SF | SR | SS | ST | SY | SZ | SAB |
|---|---|---|---|---|---|---|---|---|---|---|---|---|
| Initial Solution pH | 7.46 | 7.48 | 6.49 | 7.55 | 6.48 | 7.56 | 5.99 | 4.98 | 4.98 | 5.06 | 4.97 | 4.99 |
| Sucrose (mg/mL) | 23.6 | 19 | 19 | 38 | 38 | 38 | -- | -- | -- | -- | -- | -- |
| Glycerin (mg/mL) | -- | -- | -- | -- | -- | -- | -- | -- | -- | 9 | 18 | 14 |
| NaCl (mg/mL) | -- | -- | -- | -- | -- | -- | 4.4 | 4.1 | 6.17 | -- | -- | -- |
| Acid | AcOH | AcOH | AcOH-HCl | AcOH | AcOH-HCl | HCl | AcOH-HCl | AcOH-HCl | AcOH-HCl | AcOH-HCl | AcOH-HCl | AcOH-HCl |

| | SA | SB | SC | SD | SE | SF | SR | SS | ST | SY | SZ | SAB |
|---|---|---|---|---|---|---|---|---|---|---|---|---|
| Initial Solution pH | 7.46 | 7.48 | 6.49 | 7.55 | 6.48 | 7.56 | 5.99 | 4.98 | 4.96 | 5.06 | 4.97 | 4.99 |
| Sucrose (mg/mL) | 23.6 | 19 | 19 | 38 | 38 | 38 | -- | -- | -- | -- | -- | -- |
| Glycerin (mg/mL) | -- | -- | -- | -- | -- | -- | -- | -- | -- | 9 | 18 | 14 |
| NaCl (mg/mL) | -- | -- | -- | -- | -- | -- | 4.4 | 4.1 | 6.17 | -- | -- | -- |
| Acid | AcOH | AcOH | AcOH-HCl | AcOH | AcOH-HCl | HCl | AcOH-HCl | AcOH-HCl | AcOH-HCl | AcOH-HCl | AcOH-HCl | AcOH-HCl |

| | SA | SB | SC | SD | SE | SF | SR | SS | ST | SY | SZ | SAB |
|---|---|---|---|---|---|---|---|---|---|---|---|---|
| Initial Solution pH | 7.46 | 7.48 | 6.49 | 7.55 | 6.48 | 7.56 | 5.99 | 4.98 | 4.98 | 5.06 | 4.97 | 4.99 |
| Sucrose (mg/mL) | 23.6 | 19 | 19 | 38 | 38 | 38 | -- | -- | -- | -- | -- | -- |
| Glycerin (mg/mL) | -- | -- | -- | -- | -- | -- | -- | -- | -- | 9 | 18 | 14 |
| NaCl (mg/mL) | -- | -- | -- | -- | -- | -- | 4.4 | 4.1 | 6.17 | -- | -- | -- |
| Acid | AcOH | AcOH | AcOH-HCl | AcOH | AcOH-HCl | HCl | AcOH-HCl | AcOH-HCl | AcOH-HCl | AcOH-HCl | AcOH-HCl | AcOH-HCl |

| | SA | SB | SC | SD | SE | SF | SR | SS | ST | SY | SZ | SAB |
|---|---|---|---|---|---|---|---|---|---|---|---|---|
| Initial Solution pH | 7.46 | 7.48 | 6.49 | 7.55 | 6.48 | 7.55 | 5.99 | 4.98 | 4.98 | 5.06 | 4.97 | 4.99 |
| Sucrose (mg/mL) | 23.6 | 19 | 19 | 38 | 38 | 38 | -- | -- | -- | -- | -- | -- |
| Glycerin (mg/mL) | -- | -- | -- | -- | -- | -- | -- | -- | -- | 9 | 18 | 14 |
| NaCl (mg/mL) | -- | -- | -- | -- | -- | -- | 4.4 | 4.1 | 6.17 | -- | -- | -- |
| Acid | AcOH | AcOH | AcOH-HCl | AcOH | AcOH-HCl | HCl | AcOH-HCl | AcOH-HCl | AcOH-HCl | AcOH-HCl | AcOH-HCl | AcOH-HCl |

FIGURE 11

CERTIFICATE OF ANALYSIS

SGS

Assignment No.: 09A2016784
PO No.: C000578092
Page: 1 of 3

Product: Liquid

Identification: RUC-4 Sterile Solution, 18 mg/mL
Project: 05674P0420
Lot: 04410320 (Engineering)
Stability: T = 6M @ 2-8°C Qty Rec'd: 10

SGS Sample No.: 09620043325 Received Date: 19-Nov-2020 Procedure: USP 43

| Test/Parameter | Method | Specification | Result | Status |
|---|---|---|---|---|
| Particulate Matter - Light Obscuration (Small Volume) | USP <788> | | | Pass |
| Particle Count (≥ 10 µm) | | NMT 6000/container | 51 /container | |
| Particle Count (>=25µm) | | NMT 600/container | <1 /container | |

FIGURE 12

CERTIFICATE OF ANALYSIS

SGS

Assignment No.: 09A2016784
Page: 2 of 3

Product: Liquid

Identification: RUC-4 Sterile Solution, 18 mg/mL
Project: 05674P0420
Lot: 04410320 (Engineering)
Stability: T = 6M @ 25°C/60% RH Qty Rec'd: 10

SGS Sample No.: 09S20043326 Received Date: 19-Nov-2020 Procedure: USP 43

| Test/Parameter | Method | Specification | Result | Status |
|---|---|---|---|---|
| Particulate Matter - Light Obscuration (Small Volume) | USP <788> | | | Pass |
| Particle Count (≥ 10 µm) | | NMT 6000/container | 14 /container | |
| Particle Count (>=25µm) | | NMT 600/container | <1 /container | |

FIGURE 13

| Component | Area% | | | |
|---|---|---|---|---|
| | Initial lyophile | 25°C / 60% RH<br>4 weeks | 25°C / 60% RH<br>3 Months | 5°C<br>3 Months |
| RUC-4 | 97.14<br>97.13 | 96.27<br>96.25 | 95.17<br>95.12 | 96.88<br>96.90 |
| Des-gly | 0.47<br>0.47 | 0.50<br>0.51 | 0.58<br>0.58 | 0.48<br>0.48 |
| Bis-Gly | 1.62<br>1.61 | 1.64<br>1.63 | 1.66<br>1.66 | 1.61<br>1.61 |
| RUC-4 acetamide | 0.04<br>0.04 | 0.78<br>0.78<br>(1.02 wt%) | 1.56<br>1.60<br>(2.08 wt%) | 0.27<br>0.27 |
| RRT ~1.22 | -- | - | 0.09<br>0.09 | 0.08<br>0.08 |
| RRT ~1.49 | -- | 0.02<br>0.02 | 0.01<br>0.01 | 0.01<br>0.01 |
| RRT ~1.57 | -- | 0.11<br>0.11 | 0.24<br>0.24 | 0.04<br>0.04 |
| RRT ~1.62 | -- | 0.01<br>0.01 | 0.10<br>0.11 | 0.10<br>0.10 |

FIGURE 14

| Component | Area% | | | | |
|---|---|---|---|---|---|
| | Initial lyophile | 40°C / 75% RH 2 weeks | 40°C / 75% RH 4 weeks | 40°C / 75% RH 2 Months | 40°C / 75% RH 3 Months |
| RUC-4 | 97.14<br>97.13 | 95.06<br>95.09 | 93.76<br>93.72 | 91.2<br>91.22 | 89.57<br>89.36 |
| Des-gly | 0.47<br>0.47 | 0.59<br>0.59 | 0.64<br>0.64 | 0.79<br>0.78 | 0.88<br>0.88 |
| Bis-Gly | 1.62<br>1.61 | 1.67<br>1.67 | 1.70<br>1.70 | 1.76<br>1.76 | 1.77<br>1.77 |
| RUC-4 acetamide | 0.04<br>0.04 | 1.67<br>1.65<br>(2.18 wt%) | 2.72<br>2.74<br>(3.59 wt%) | 4.6<br>4.6<br>(6.04 wt%) | 5.78<br>6.03<br>(7.76 wt%) |
| RRT ~1.22 | -- | -- | 0.05<br>0.05 | 0.08<br>0.08 | 0.11<br>0.11 |
| RRT ~1.49 | -- | -- | 0.03<br>0.04 | 0.05<br>0.05 | 0.06<br>0.06 |
| RRT ~1.57 | -- | -- | 0.42<br>0.42 | 0.72<br>0.72 | 0.91<br>0.91 |
| RRT ~1.62 | -- | -- | 0.02<br>0.02 | 0.08<br>0.08 | 0.10<br>0.10 |

FIGURE 15

| Component | Area% | | | |
|---|---|---|---|---|
| | Initial lyophile | 25°C / 60% RH<br>4 weeks | 25°C / 60% RH<br>3 Months | 5°C<br>3 Months |
| RUC-4 | 97.20<br>97.19 | 97.04<br>97.00 | 96.79<br>96.74 | 97.17<br>97.15 |
| Des-gly | 0.46<br>0.46 | 0.47<br>0.45 | 0.48<br>0.49 | 0.46<br>0.46 |
| Bis-Gly | 1.61<br>1.60 | 1.63<br>1.61 | 1.60<br>1.61 | 1.60<br>1.59 |
| RUC-4 acetamide | 0.01<br>0.01 | 0.15<br>0.16 | 0.35<br>0.36<br>(0.47 wt%) | 0.08<br>0.07 |
| RRT ~1.22 | -- | - | 0.08<br>0.08 | 0.07<br>0.07 |
| RRT ~1.49 | -- | - | 0.01<br>0.01 | 0.01<br>0.01 |
| RRT ~1.57 | -- | 0.03<br>0.03 | 0.08<br>0.08 | 0.08<br>0.08 |
| RRT ~1.62 | -- | 0.01<br>0.01 | 0.10<br>0.10 | 0.09<br>0.11 |

FIGURE 16

| Component | Area% | | | | |
|---|---|---|---|---|---|
| | Initial lyophile | 40°C / 75% RH 2 weeks | 40°C / 75% RH 4 weeks | 40°C / 75% RH 2 Months | 40°C / 75% RH 3 Months |
| RUC-4 | 97.20<br>97.19 | 96.74<br>96.77 | 96.44<br>96.43 | 95.76<br>95.86 | 95.34<br>95.35 |
| Des-gly | 0.46<br>0.46 | 0.49<br>0.49 | 0.50<br>0.49 | 0.54<br>0.53 | 0.57<br>0.56 |
| Bis-Gly | 1.61<br>1.60 | 1.60<br>1.60 | 1.61<br>1.61 | 1.62<br>1.61 | 1.60<br>1.61 |
| RUC-4 acetamide | 0.01<br>0.01 | 0.37<br>0.37<br>(0.49 wt%) | 0.61<br>0.61<br>(0.80 wt%) | 1.06<br>1.02<br>(1.37 wt%) | 1.38<br>1.41<br>(1.83 wt%) |
| RRT ~1.22 | -- | -- | 0.02<br>0.02 | 0.03<br>0.03 | 0.09<br>0.09 |
| RRT ~1.49 | -- | -- | 0.02<br>0.02 | 0.01<br>0.01 | 0.01<br>0.00 |
| RRT ~1.57 | -- | -- | 0.14<br>0.14 | 0.23<br>0.24 | 0.32<br>0.32 |
| RRT ~1.62 | -- | -- | 0.01<br>0.01 | 0.09<br>0.09 | 0.10<br>0.10 |

RUC-4 FORMULATIONS

RELATED APPLICATIONS

This application is a National Stage filing under 35 U.S.C. 371 of International PCT Application No. PCT/US2022/016564, filed Feb. 16, 2022, which claims priority under 35 U.S.C. § 119 (e) to U.S. Provisional Application No. 63/150,168, filed Feb. 17, 2021, the contents of which are incorporated herein by reference in their entirety.

BACKGROUND

RUC-4 is an inhibitor of the platelet αIIbβ3 receptor and is described in U.S. Pat. No. 9,303,044, which is incorporated herein by reference. In the present disclosure, RUC-4 is referred to as Compound (1). There is a need for solid and liquid formulations of RUC-4 that are stable under a range of storage conditions.

SUMMARY

In one aspect, provided herein is a composition comprising Compound (1):

(1)

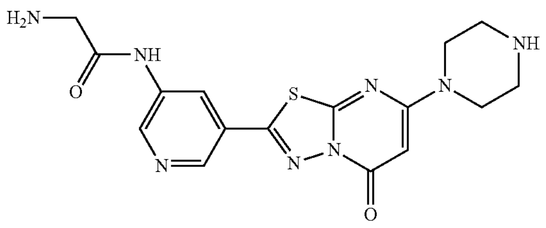

and acetic acid. In certain embodiments, the molar ratio of Compound (1) to acetic acid is about 1:2. In certain embodiments, the composition comprises an additional acid or acids. In certain embodiments, the composition further comprises additional excipients or additives which adjust properties such as osmolality and stability. In certain embodiments, the composition is a chemically and physically stable solution.

In another aspect, provided herein is a composition comprising Compound (1) in the form of an addition salt with acetic acid. In certain embodiments, the molar ratio of Compound (1) to acetic acid is in the range of about 1:0.5 to about 1:3. In certain embodiments, the composition is a lyophilized solid.

In another aspect, provided herein is a method of making a lyophilized composition, comprising: preparing a solution comprising Compound (1) and acetic acid; filtering the solution; freezing the solution; and removing the water from the frozen solution by sublimation at low pressure. In certain embodiments, the solution comprises an additional acid or acids. In certain embodiments, the solution further comprises additional excipients or additives which adjust properties such as osmolality and stability.

In another aspect, provided herein is a method of making a solution of Compound (1) for administration by injection, comprising contacting Compound (1), or a pharmaceutically acceptable salt thereof, or a lyophilized composition as described herein, with a pharmaceutically acceptable solvent in a vial, a syringe, or an autoinjector.

BRIEF DESCRIPTION OF THE DRAWINGS

FIG. 11 depicts the stability report for Formulation 1 after storage for 6 months at 2-8° C.

FIG. 12 depicts the stability report for Formulation 1 after storage for 6 months at 25° C./60% RH.

FIG. 13 depicts lyophilization stability data at 25° C./60% RH and 5° C. Formulations: In a 5 mL vial, 110 mg Compound (1), 1:1.1 molar ratio of Compound (1) to acetic acid, and 2 mL sterile water for injection (SWFI). Samples were frozen at −45° C. and dried at −25° C. for 39 hours at 100-150 mTorr, then at ambient temperature for an additional 5 hours.

FIG. 14 depicts lyophilization stability data at 40° C./75% RH. Formulations: In a 5 mL vial, 110 mg Compound (1), 1:1.1 molar ratio of Compound (1) to acetic acid, and 2 mL SWFI. Samples were frozen at −45° C. and dried at −25° C. for 39 hours at 100-150 mTorr, then at ambient temperature for an additional 5 hours.

FIG. 15 depicts lyophilization stability data at 25° C./60% RH and 5° C. Formulations: In a 5 mL vial, 110 mg Compound (1), 1:1.1 molar ratio of Compound (1) to acetic acid, 47.2 mg sucrose, and 2 mL SWFI. Samples were frozen at −45° C. and dried at −25° C. for 39 hours at 100-150 mTorr, then at ambient temperature for an additional 5 hours.

FIG. 16 depicts lyophilization stability data at 40° C./75% RH. Formulations: In a 5 mL vial, 110 mg Compound (1), 1:1.1 molar ratio of Compound (1) to acetic acid, 47.2 mg sucrose, and 2 mL SWFI. Samples were frozen at −45° C. and dried at −25° C. for 39 hours at 100-150 mTorr, then at ambient temperature for an additional 5 hours.

DETAILED DESCRIPTION

Figure 1:
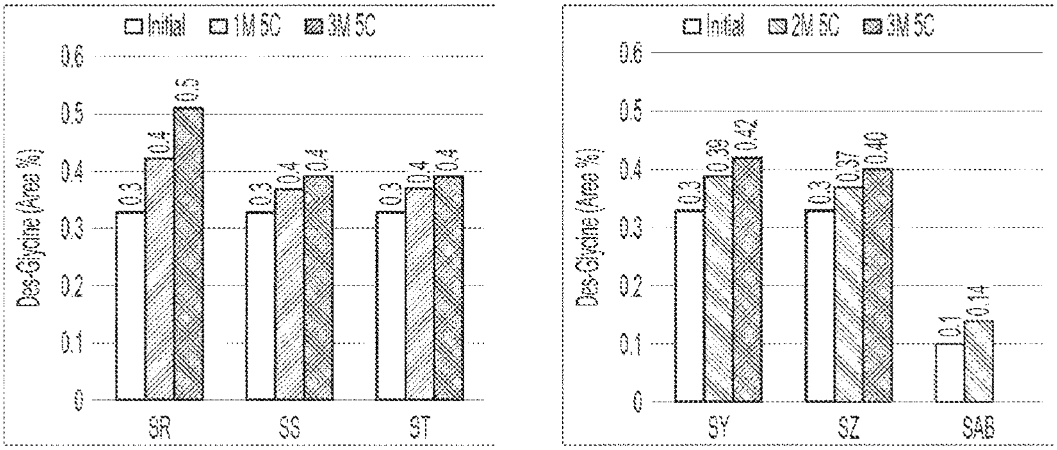
FIG. 1 depicts levels of des-glycine decomposition product observed in the formulations of Table 4 upon preparation (initially), after 1 month storage at 5° C., and after 3 months storage at 5° C.
Figure 2:
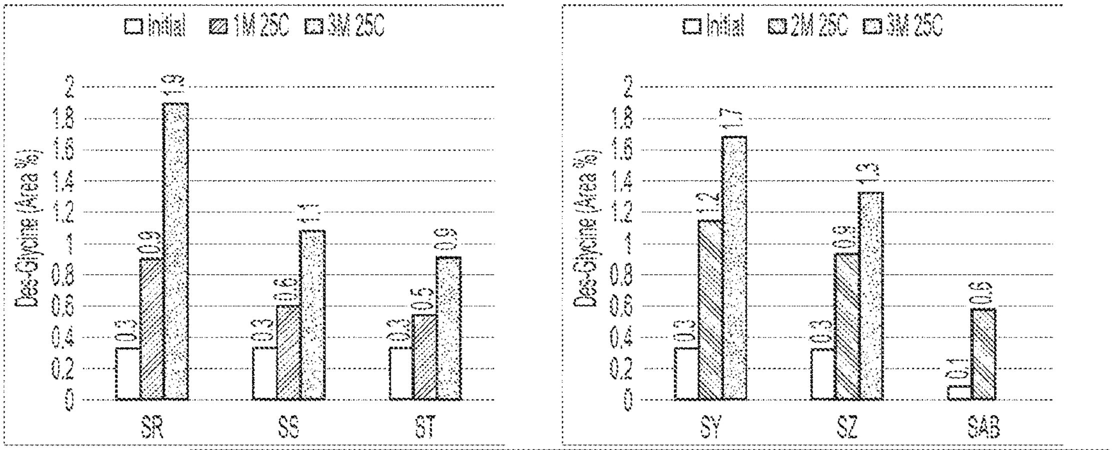
FIG. 2 depicts levels of des-glycine decomposition product observed in the formulations of Table 4 upon preparation (initially), and after 1, 2, or 3 months storage at 25° C./60% RH.
Figure 3:
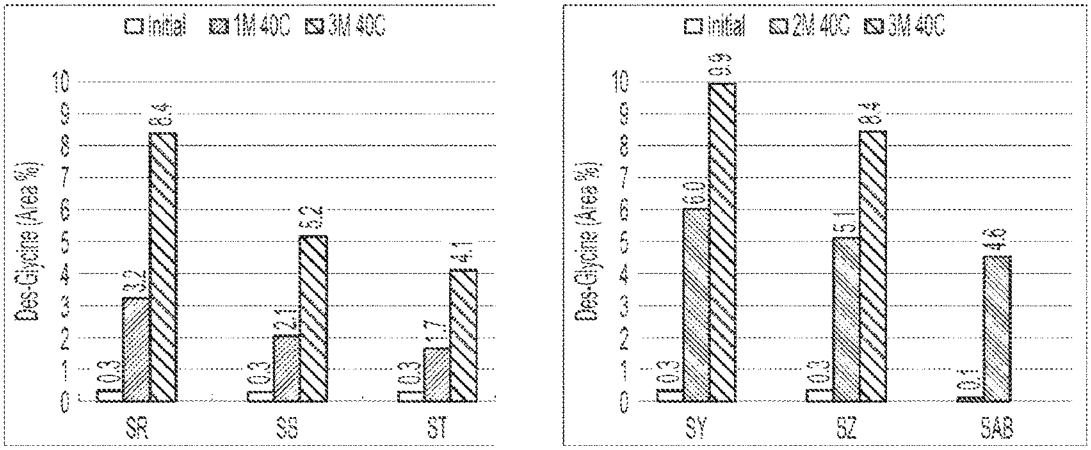
FIG. 3 depicts levels of des-glycine decomposition product observed in the formulations of Table 4 upon preparation (initially), and after 1, 2, or 3 months storage at 40° C./75% RH.
Figure 4:
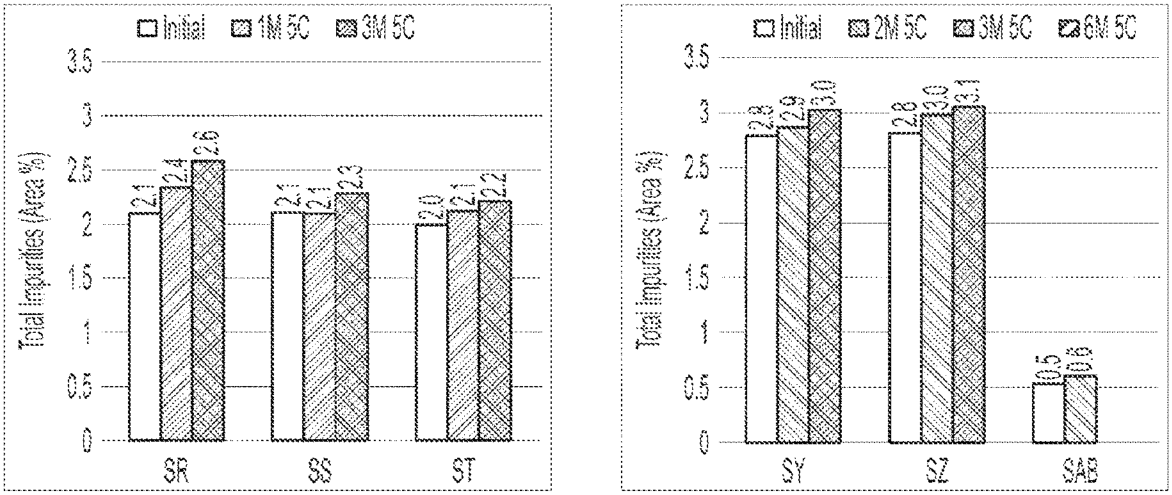
FIG. 4 depicts total impurity levels observed in the formulations of Table 4 upon preparation (initially), and after 1, 2, or 3 months storage at 5° C.
Figure 5:
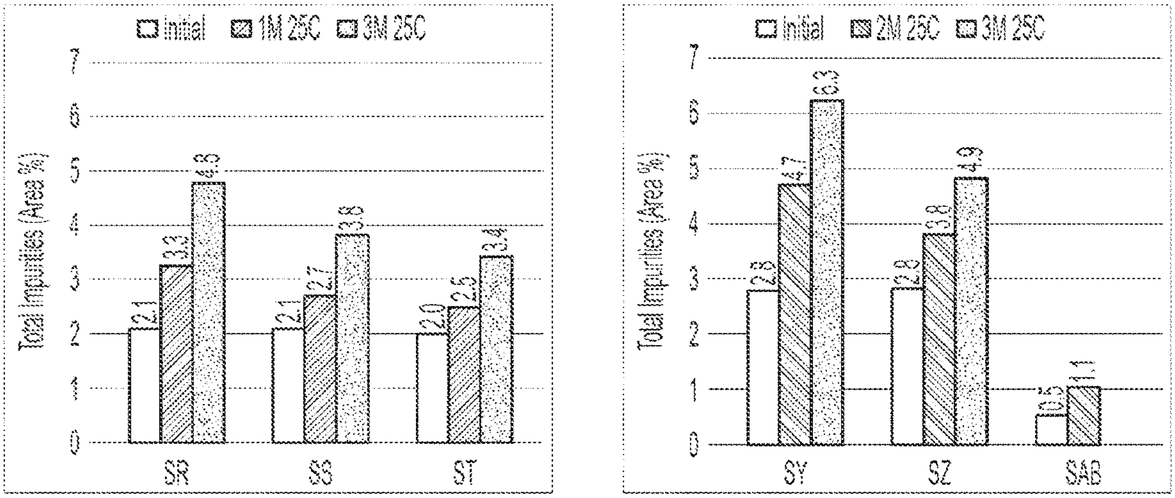
FIG. 5 depicts total impurity levels observed in the formulations of Table 4 upon preparation (initially), and after 1, 2, or 3 months storage at 25° C.
Figure 6:
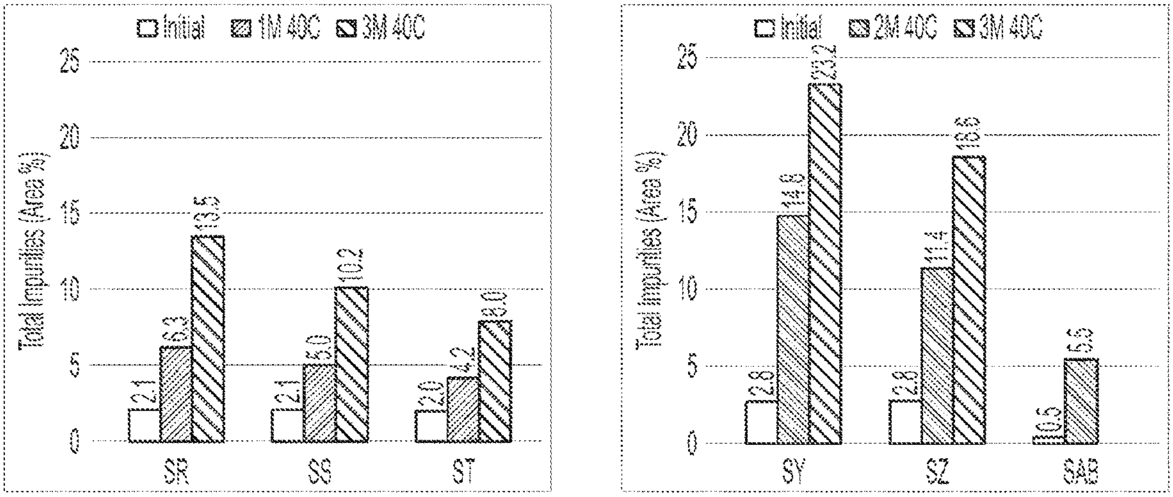
FIG. 6 depicts total impurity levels observed in the formulations of Table 4 upon preparation (initially), and after 1, 2, or 3 months storage at 40° C.
Figure 7:
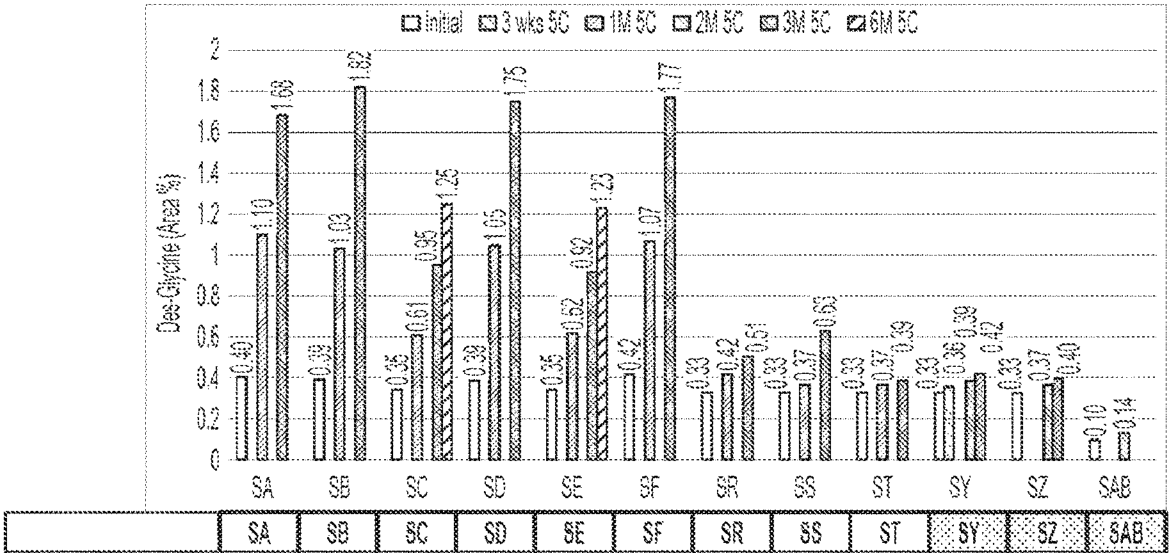
FIG. 7 depicts levels of des-glycine decomposition product observed in formulations upon preparation (initially), and after 3 weeks, and 1, 2, 3, or 6 months storage at 5° C.
Figure 8:
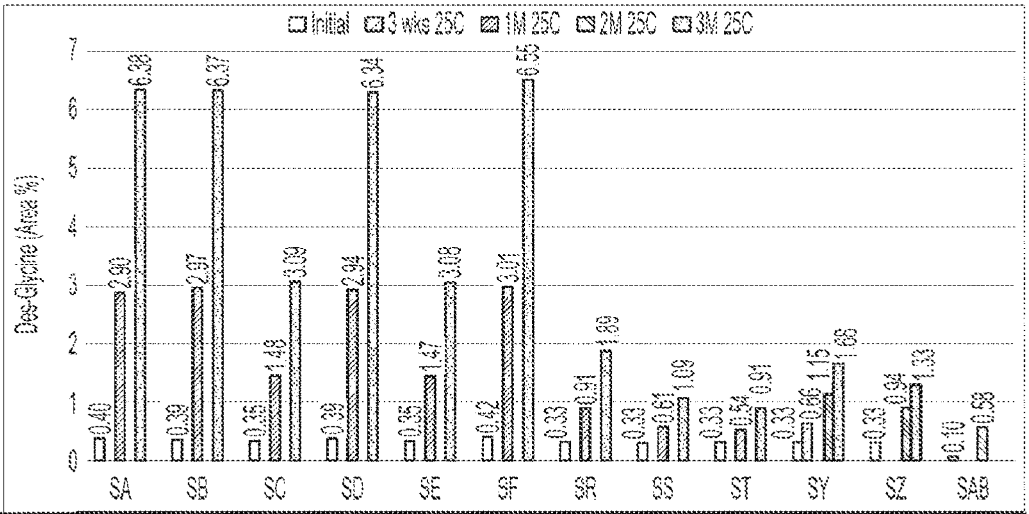
FIG. 8 depicts levels of des-glycine decomposition product observed in formulations upon preparation (initially), and after 3 weeks, and 1, 2, or 3 months storage at 25° C./60% RH.
Figure 9:
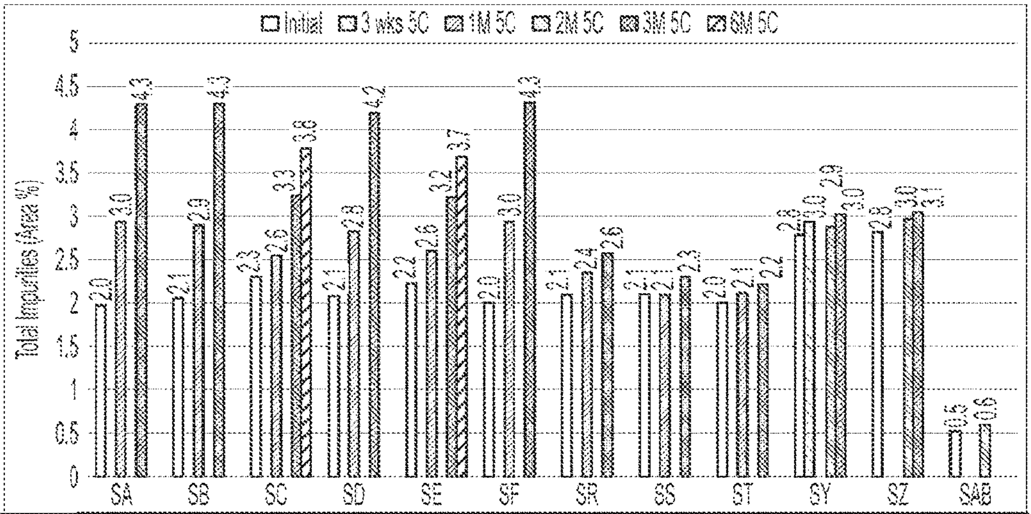
FIG. 9 depicts total impurity levels observed in formulations upon preparation (initially), and after 3 weeks, and 1, 2, 3, or 6 months storage at 5° C.
Figure 10:
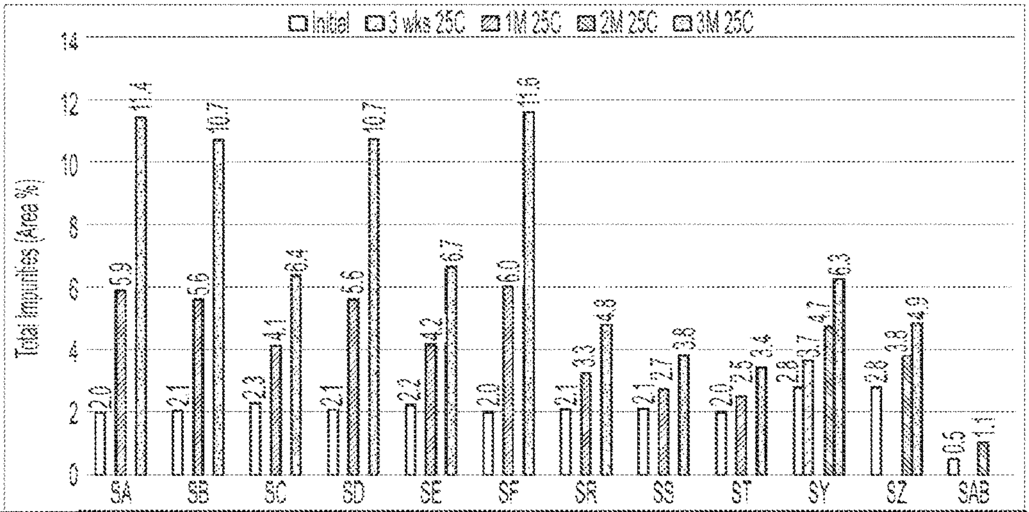
FIG. 10 depicts total impurity levels observed in formulations upon preparation (initially), and after 3 weeks, and 1, 2, or 3 months storage at 25° C./60% RH.

The present disclosure is based, in part, on the discovery of the surprisingly high solubility of Compound (1) in acetic acid. In particular, solutions of greater than 300 mg/mL are obtainable.

The present disclosure provides stable compositions comprising Compound (1):

(1)

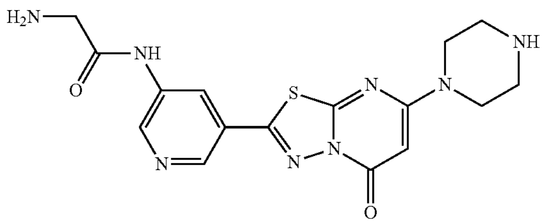

and acetic acid.

In certain embodiments, the compositions comprise an additional acid, which may act as a solubilizer, pH adjustor, or stabilizer. In certain embodiments, the additional acid is one or more of a pharmaceutically acceptable organic acid and/or a pharmaceutically acceptable inorganic acid.

In certain embodiments, provided herein is a composition comprising Compound (1), acetic acid, and hydrochloric acid. In certain embodiments, the molar ratio of Compound (1) to acetic acid is about 1:2.4, about 1:2.2, about 1:2, about 1:1.9, about 1:1.8, about 1:1.6, about 1:1.4, about 1:1.2, about 1:1, about 1:0.8, about 1:0.6, or about 1:0.4.

In certain embodiments, provided herein is a composition comprising Compound (1), acetic acid, hydrochloric acid, and citric acid. In certain embodiments, the molar ratio of Compound (1) to acetic acid is about 1:2.4, about 1:2.2, about 1:2, about 1:1.9, about 1:1.8, about 1:1.6, about 1:1.4, about 1:1.2, about 1:1, about 1:0.8, about 1:0.6, or about 1:0.4.

In certain embodiments, the composition is a solution comprising water. In certain embodiments, the pH is about 4.0-6.0, inclusive. In certain embodiments, the solution has a pH of about 4.25-6.0, inclusive. In certain embodiments, the pH is about 4.0-5.0, inclusive. In certain embodiments, the pH is about 4.25-4.75, inclusive. In certain embodiments, the pH is about 4.5-5.5, inclusive. In certain embodiments, the pH is about 4.75-5.25, inclusive. In certain embodiments, the pH is about 4.5-5.0, inclusive.

In certain embodiments, the composition is a solution and the total chloride ion concentration in the composition is ≤35 mM. In certain particular embodiments, the total chloride ion concentration is about 5-35 mM, about 10-30 mM, about 15-25 mM, about 20-35 mM, or about 25-35 mM. In certain embodiments, the solution comprises an additional pharmaceutically acceptable solvent. In certain embodiments, the composition is a solution in a solvent comprising water and another pharmaceutically acceptable solvent.

In certain embodiments, the composition is a solution of Compound (1) and acetic acid in water, further comprising an additional acid that is not hydrochloric acid. In certain embodiments, the concentration of the additional acid is ≤35 mM. In certain particular embodiments, the concentration of the additional acid is about 5-35 mM, about 10-30 mM, about 15-25 mM, about 20-35 mM, or about 25-35 mM.

In certain embodiments, the composition is a solution comprising water having an osmolality of ≥200 mmol/L. In certain particular embodiments, the osmolality is about 200-250 mmol/L, about 250-300 mmol/L, about 300-350 mmol/L, or about 350-400 mmol/L. In certain embodiments, the composition further comprises one or more osmotic agents, including, but not limited to salts and polyols (including, e.g., sugars).

In certain embodiments, the composition is a solution comprising about 1-500 mg/mL of Compound (1). In certain embodiments, the composition comprises about 1-400 mg/ml of Compound (1). In certain embodiments, the composition comprises about 1-300 mg/ml of Compound (1). In certain embodiments, the composition comprises about 1-200 mg/mL of Compound (1). In certain embodiments, the composition comprises about 1-100 mg/mL of Compound (1). In certain embodiments, the composition is a solution comprising about 1-50 mg/mL of Compound (1). In certain embodiments, the composition comprises about 5-25 mg/mL of Compound (1). In certain embodiments, the composition comprises about 10-25 mg/mL of Compound (1). In certain embodiments, the composition comprises about 10-20 mg/mL of Compound (1). In certain embodiments, the composition comprises about 12-20 mg/mL of Compound (1). In certain embodiments, the composition comprises about 15-20 mg/mL of Compound (1). In certain embodiments, the composition comprises about 12-18 mg/mL of Compound (1). In certain embodiments, the composition comprises about 15-18 mg/mL of Compound (1).

In certain embodiments, the composition comprises 1-20 mg/mL of acetic acid. In certain embodiments, the composition comprises 1-15 mg/mL of acetic acid. In certain embodiments, the composition comprises 1-10 mg/mL of acetic acid. In certain embodiments, the composition comprises 3-8 mg/mL of acetic acid. In certain embodiments, the composition comprises 3-7 mg/mL of acetic acid. In certain embodiments, the composition comprises 3-6 mg/mL of acetic acid. In certain embodiments, the composition comprises 4-8 mg/mL of acetic acid. In certain embodiments, the composition comprises 4-7 mg/mL of acetic acid. In certain embodiments, the composition comprises 4-6 mg/mL of acetic acid. In certain embodiments, the composition comprises 5-8 mg/mL of acetic acid. In certain embodiments, the composition comprises 5-7 mg/mL of acetic acid. In certain embodiments, the composition comprises 5-6 mg/mL of acetic acid. In certain embodiments, the composition comprises 10-20 mg/mL of acetic acid. In certain embodiments, the composition comprises 10-15 mg/mL of acetic acid. In certain embodiments, the composition comprises 15-20 mg/mL of acetic acid. In certain embodiments, the composition comprises about 1 mg/mL of acetic acid. In certain embodiments, the composition comprises about 2 mg/mL of acetic acid. In certain embodiments, the composition comprises about 3 mg/mL of acetic acid. In certain embodiments, the composition comprises about 4 mg/mL of acetic acid. In certain embodiments, the composition comprises about 5 mg/mL of acetic acid. In certain embodiments, the composition comprises about 6 mg/mL of acetic acid. In certain embodiments, the composition comprises about 7 mg/mL of acetic acid. In certain embodiments, the composition comprises about 8 mg/mL of acetic acid. In certain embodiments, the composition comprises about 9 mg/mL of acetic acid. In certain embodiments, the composition comprises about 10 mg/mL of acetic acid. In certain embodiments, the composition comprises about 11 mg/mL of acetic acid. In certain embodiments, the composition comprises about 12 mg/mL of acetic acid. In certain embodiments, the composition comprises about 13 mg/mL of acetic acid. In certain embodiments, the composition comprises about 14 mg/mL of acetic acid. In certain embodiments, the composition comprises about 15 mg/mL of acetic acid. In certain embodiments, the composition comprises about 16 mg/mL of acetic acid. In certain embodiments, the composition comprises about 17 mg/mL of acetic acid. In certain embodiments, the composition comprises about 18 mg/mL of acetic acid. In certain embodiments, the composition comprises about 19 mg/mL of acetic acid. In certain embodiments, the composition comprises about 20 mg/mL of acetic acid.

In certain embodiments, the composition comprises 1-10 mg/mL of citric acid. In certain embodiments, the composition comprises 3-8 mg/mL of citric acid. In certain embodiments, the composition comprises 5-8 mg/mL of citric acid. In certain embodiments, the composition comprises 3-5 mg/mL of citric acid. In certain particular embodiments, the composition comprises 0-3 mg/mL of citric acid. In certain embodiments, the composition comprises 1-3 mg/mL of citric acid. In certain embodiments, the composition comprises 1-2 mg/mL of citric acid. In certain embodiments, the composition comprises about 2 mg/ml of citric acid. In certain embodiments, the composition comprises about 1.35 mg/mL of citric acid. In certain embodiments, the composition comprises about 1 mg/mL of citric acid.

In certain embodiments, the composition further comprises a polyol. In certain embodiments, the polyol is glycerin, i.e., glycerol. In certain embodiments, the polyol is propylene glycol. In certain embodiments, the composition comprises about 1-50 mg/mL polyol. In certain embodiments, the composition comprises about 10-30 mg/mL polyol. In certain embodiments, the composition comprises about 10-20 mg/mL polyol. In certain embodiments, the composition comprises about 12-18 mg/mL polyol.

In certain embodiments, the polyol is a sugar. In certain particular embodiments, the sugar is sucrose. In certain particular embodiments, the sugar is mannitol. In certain particular embodiments, the sugar is trehalose.

In certain embodiments, the composition further comprises one or more additional agents, such as a buffering agent, a tonicity agent, a stabilizing agent, or a solubilizing agent.

The effect of various formulation components on stability is shown in Tables 1-2. FIGS. 1-10 show specific impurity levels or total impurity levels.

TABLE 1

| Formulations and Stabilities | | | | | | | |
|---|---|---|---|---|---|---|---|
| Formula | R | S | T | Z | Y | AA | AB |
| RUC-4, free base | 22 mg | 22 mg | 10 mg | 10 mg | 22 mg | 22 mg | 18 mg |
| Acetic acid USP | 3.76 mg | 3.76 mg | 1.71 mg | 3.11 mg | 6.83 mg | 6.83 mg | 5.59 mg |
| Hydrochloric acid | qs to pH 6.0 ± 0.1 | qs to pH 5.0 ± 0.1 | qs to pH 5.0 ± 0.1 | qs to pH 5.0 ± 0.1 | qs to pH 5.0 ± 0.1 | qs to pH 5.0 ± 0.1 | qs to pH 5.0 ± 0.1 |
| Glycerin USP | — | — | — | 18 mg | 9 mg | 10 mg | 14 mg |
| Sodium chloride USP | 4.4 mg | 4.1 mg | 6.17 mg | — | — | — | — |
| Water for Injection USP | qs to 1 mL | qs to 1 mL | qs to 1 mL | qs to 1 mL | qs to 1 mL | qs to 1 mL | qs to 1 mL |
| Solution pH | 5.99 | 4.98 | 4.98 | 5.07 | 5.06 | 5.05 | 4.99 |
| Solution Osmolality mOsm/kg | 273 | 280 | 269 | 287 | 263 | 258 | 284 |
| Refrigerated (5° C.) | Precipitate in 1 min. | Precipitate in 1 min. | Precipitate in 1 min. | Clear solution at 3.5 weeks | Precipitate in 3 weeks | Clear solution at 2.5 weeks | Clear solution at 6 weeks |

TABLE 2

| Formulations and Stabilities | | | |
|---|---|---|---|
| Formula | A | B | C |
| RUC-4, free base | 18.0 mg/mL | 18.0 mg/mL | 18.0 mg/mL |
| Acetic acid USP | 5.6 mg/mL | 5.6 mg/mL | 5.6 mg/mL |
| Anhydrous Citric acid USP | 1.35 mg/mL | 1.35 mg/mL | 1.35 mg/mL |
| Glycerin USP | 16.0 mg/mL | 15.0 mg/mL | 14.0 mg/mL |
| Hydrochloric acid | qs to pH 4.75 (25.6 mM added) | qs to pH 4.50 (38.4M added) | qs to pH 4.25 (54 mM added) |
| Water for Injection USP | qs to 1 mL | qs to 1 mL | qs to 1 mL |
| Appearance | Clear pale-yellow solution | Clear pale-yellow solution | Clear pale-yellow solution |
| Solution pH | 4.77 | 4.50 | 4.26 |
| Solution Osmolality mOsm/kg | 304 | 303 | 304 |

In certain embodiments, a composition as described herein further comprises Compound (2):

(2)

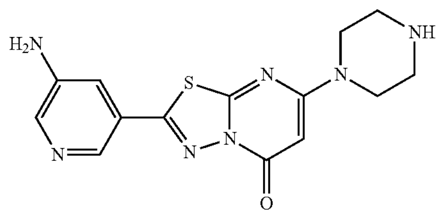

or a salt thereof. In certain embodiments, Compound (2) is present in an amount that is less than about 10% by weight, less than about 8% by weight, less than about 6% by weight, less than about 4% by weight, less than about 2% by weight, or less than about 1% by weight of the composition.

In certain embodiments, a composition as described herein further comprises Compound (3):

(3)

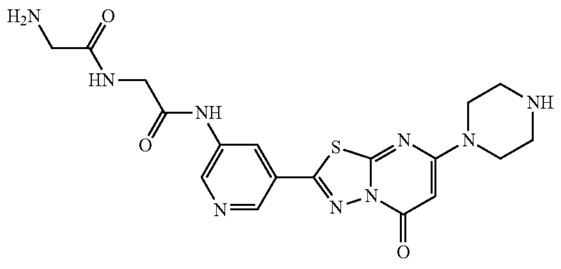

or a salt thereof. In certain embodiments, Compound (3) is present in an amount that is less than about 10% by weight, less than about 8% by weight, less than about 6% by weight, less than about 4% by weight, less than about 2% by weight, or less than about 1% by weight of the composition.

In certain particular embodiments, provided herein are compositions comprising the following components per milliliter of water.

(1) Formulation 1 (pH of 5.0±0.1)

| | |
|---|---|
| Compound (1) | 18 mg |
| Acetic acid | 5.59 mg |
| Hydrochloric acid | qs to pH 5.0 ± 0.1 |
| Glycerin | 14 mg |

(2) Formulation 2 (pH of 4.75±0.1)

| | |
|---|---|
| Compound (1) | 17.5 mg |
| Acetic acid | 5.43 mg |
| Hydrochloric acid | 1.53 mg |
| Glycerin | 14.6 mg |

(3) Formulation 3 (pH of 4.75±0.1)

| | |
|---|---|
| Compound (1) | 15 mg |
| Acetic acid | 4.66 mg |
| Hydrochloric acid | 1.31 mg |
| Glycerin | 16.3 mg |

(4) Formulation 4 (pH of 5.0±0.1)

| | |
|---|---|
| Compound (1) | 15 mg |
| Acetic acid | 4.66 mg |
| Hydrochloric acid | 0.88 mg |
| Glycerin | 18.5 mg |

(5) Formulation 5 (pH of 4.75±0.1)

| | |
|---|---|
| Compound (1) | 18 mg |
| Acetic acid | 5.6 mg |
| Anhydrous Citric Acid | 1.35 mg |
| Hydrochloric acid | 0.93 mg (QS pH to 4.75) |
| Glycerin | 16 mg |

(6) Formulation 6 (pH of 4.5±0.1)

| | |
|---|---|
| Compound (1) | 18 mg |
| Acetic acid | 5.6 mg |
| Anhydrous Citric Acid | 1.35 mg |
| Hydrochloric acid | 1.4 mg (QS pH to 4.5) |
| Glycerin | 16.3 mg |

(7) Formulation 7 (pH of 4.25±0.1)

| | |
|---|---|
| Compound (1) | 18 mg |
| Acetic acid | 5.6 mg |
| Anhydrous Citric Acid | 1.35 mg |
| Hydrochloric acid | 1.97 mg (QS pH to 4.25) |
| Glycerin | 18.5 mg |

In certain embodiments, a composition as described herein is stable for at least 1 month at 25° C./60% relative humidity (RH). In certain embodiments, a composition as described herein is stable for at least 3 months at 25° C./60% RH. In certain embodiments, a composition as described herein is stable for at least 6 months at 25° C./60% RH. In certain embodiments, a composition as described herein is stable for at least 6-18 months at 25° C./60% RH. In certain embodiments, a composition as described herein is stable for at least 6-12 months at 25° C./60% RH. In certain embodiments, a composition as described herein is stable for at least 12-24 months at 25° C./60% RH.

In certain embodiments, a composition as described herein is stable for at least 1 year at 5° C. In certain embodiments, a composition as described herein is stable for at least 2 years at 5° C. In certain embodiments, a composition as described herein is stable for at least 3 years at 5° C. In certain embodiments, a composition as described herein is stable for at least 4 years at 5° C. In certain embodiments, a composition as described herein is stable for at least 5 years at 5° C.

In certain embodiments, a liquid composition (e.g., a solution) described herein is formulated for injection. In certain embodiments, the injection is intramuscular injection. In certain embodiments, the injection is subcutaneous injection, e.g. to the arm, leg, thigh, back, buttocks, and abdomen. In certain embodiments, the injection is by a pre-filled syringe, pen, or autoinjector. In certain embodiments, the injection is self-administration by auto-injector.

In certain embodiments, the volume of the injection is 2 mL or less. In certain embodiments, the volume of the injection is 1 mL or less, e.g., about 0.9 mL, about 0.8 mL, about 0.7 mL, about 0.6 mL, about 0.5 mL, about 0.4 mL, about 0.3 mL, about 0.2 mL, or about 0.1 mL.

In another aspect, provided herein is a composition comprising Compound (1):

(1)

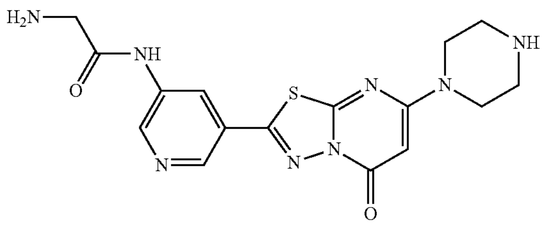

in the form of a salt of acetic acid. In certain embodiments, the molar ratio of Compound (1) to acetic acid is in the range of about 1:0.2 to about 1:2.5. In certain embodiments, the molar ratio of Compound (1) to acetic acid is in the range of about 1:0.2 to about 1:3.5. In certain embodiments, the molar ratio of Compound (1) to acetic acid is about 1:0.25. In certain embodiments, the molar ratio of Compound (1) to acetic acid is about 1:0.5. In certain embodiments, the molar ratio of Compound (1) to acetic acid is about 1:1. In certain embodiments, the molar ratio of Compound (1) to acetic acid is about 1:2. In certain embodiments, the molar ratio of Compound (1) to acetic acid is about 1:2.5. In certain embodiments, the molar ratio of Compound (1) to acetic acid is about 1:3. In certain embodiments, the molar ratio of Compound (1) to acetic acid is about 1:3.5.

In certain embodiments, the composition further comprises a polyol. In certain embodiments, the polyol is a sugar. In certain embodiments, the sugar is a non-reducing sugar. In certain embodiments, the non-reducing sugar is sucrose. In certain particular embodiments, the sugar is sucrose, trehalose, or mannitol. In certain embodiments, the molar ratio of Compound (1) to the sugar is in the range of about 2:1 to about 1:2. In certain embodiments, the molar ratio is in the range of about 2:1 to about 1:1. In certain embodiments, the molar ratio is in the range of about 1.5:1 to about 1:1.

In certain embodiments, the composition is a solution in water. In certain embodiments, the solution is intended for lyophilization. In certain embodiments, the solution is a reconstituted lyophile, wherein the lyophile is as described herein. In certain embodiments, the reconstituted lyophile further comprises sodium chloride.

In certain embodiments, the composition is a solid lyophile.

Figure 17:
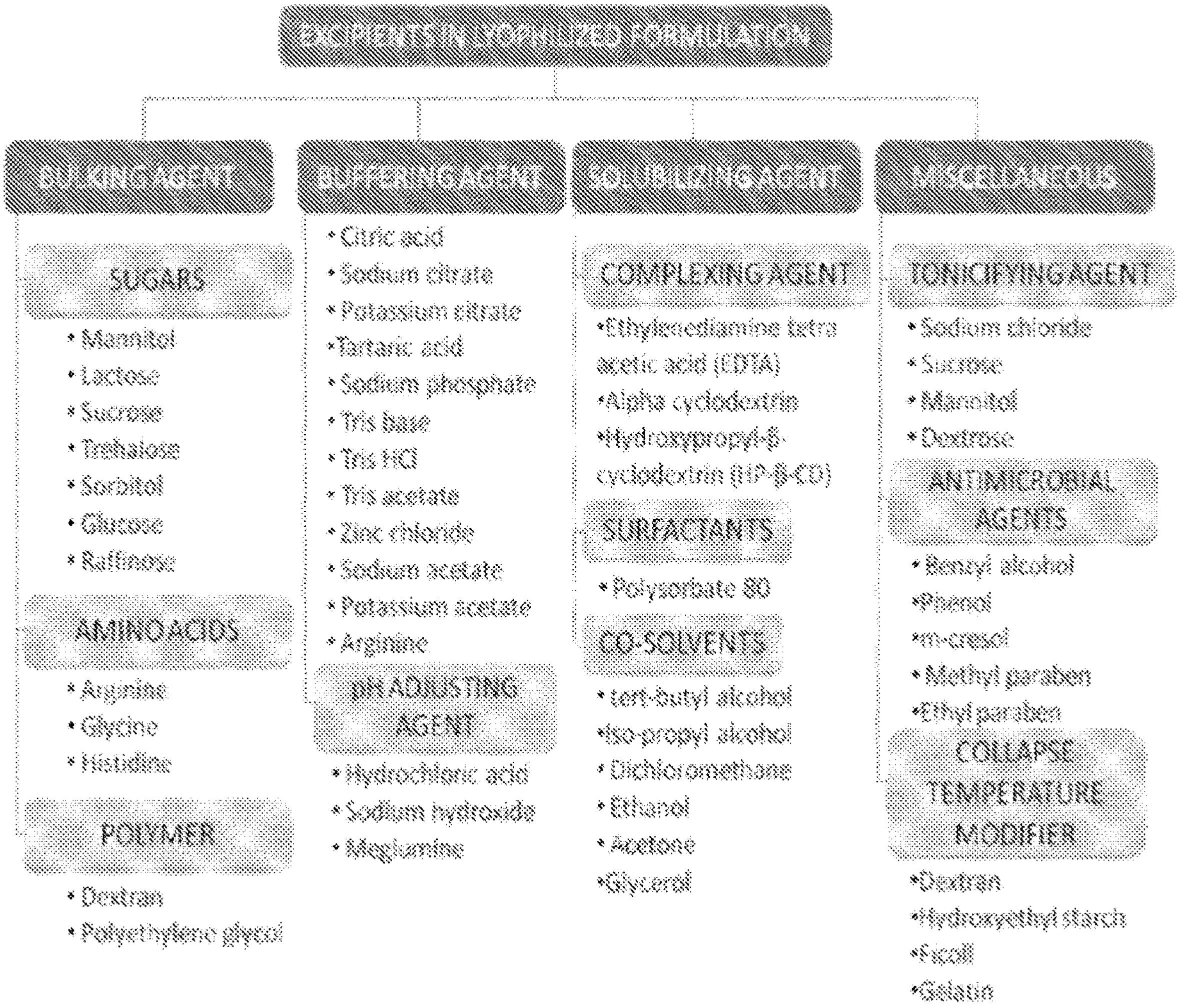
FIG. 17 depicts exemplary excipients for use in a lyophilized formulation, including bulking agents, buffering agents, solubilizing agents, and miscellaneous.

Other excipients are known in the art. Such excipients include bulking agents, buffering agents, tonicity modifiers, antimicrobial agents, and solubilizing agents. Representative excipients which may be used in lyophilized formulations are depicted in FIG. 17. See also, A. Baheti, et al. *J. Excipients and Food Chem.* 1 (1) 2010.

In certain embodiments, the composition is a spray-dried solid. In certain embodiments, the composition is a micronized solid.

In certain embodiments, a composition as described herein comprises less than 25% by weight of Compound (4):

(4)

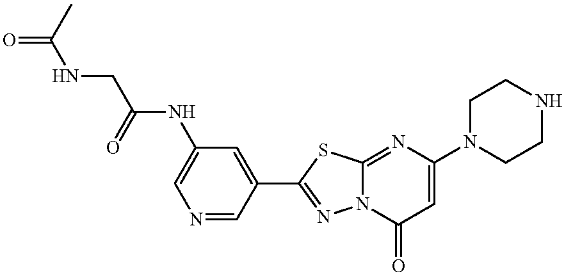

or a salt thereof.

In certain embodiments, the composition comprises less than about 20% by weight, less than about 15% by weight, less than about 10% by weight, less than about 5% by weight, less than about 4% by weight, less than about 3% by weight, less than about 2% by weight, less than about 1% by weight, or less than about 0.5% by weight of Compound (4), or a salt thereof. In any of the preceding embodiments, the composition comprises a detectable amount of Compound (4) or a salt thereof.

In certain embodiments, the composition is stable for at least 1 month at 25° C./60% RH. In certain embodiments, the composition is stable for at least 3 months at 25° C./60% RH. In certain embodiments, the composition is stable for at least 6 months at 25° C./60% RH. In certain embodiments, the composition is stable for at least 6-18 months at 25° C./60% RH. In certain embodiments, a composition as described herein is stable for at least 6-12 months at 25° C./60% RH. In certain embodiments, a composition as described herein is stable for at least 12-24 months at 25° C./60% RH.

In certain embodiments, the composition is stable for at least 1 year at 5° C. In certain embodiments, the composition is stable for at least 2 years at 5° C. In certain embodiments, the composition is stable for at least 3 years at 5° C. In certain embodiments, the composition is stable for at least 4 years at 5° C. In certain embodiments, the composition is stable for at least 5 years at 5° C.

In another aspect, provided herein is a method of making a lyophilized composition (i.e., a lyophile) as described herein, comprising: preparing a solution comprising Compound (1) and acetic acid; filtering the solution; freezing the solution; and removing the water from the frozen solution by sublimation at low pressure. In certain embodiments, the solution further comprises an additional component, such as one or more inorganic and/or organic acids, buffering agent, polyol (e.g., sugar), or preservative. In certain embodiments, the solution comprises Compound (1), acetic acid, and a non-reducing sugar. In certain embodiments, the non-reducing sugar is sucrose. In certain embodiments, solution is frozen at a temperature between −10° C. and −78° C.

In another aspect, provided herein is a method of making a solution of Compound (1) for administration by injection, comprising contacting Compound (1), or a pharmaceutically acceptable salt thereof, or a lyophilized composition (i.e., a lyophile) as described herein, with a pharmaceutically acceptable solvent in a suitable vessel, such as a vial, a syringe, or an autoinjector. In certain embodiments, the syringe is a single chamber syringe. In certain embodiments, the syringe is a dual chamber syringe. An example of a suitable dual chamber syringe is the Companion® safety syringe, manufactured by Credence MedSystems.

In certain embodiments, Compound (1), or the pharmaceutically acceptable salt thereof, or the lyophilized composition, is present in the syringe prior to contact with the solvent. In certain embodiments, the pharmaceutically acceptable solvent comprises sterile water for injection, saline, or other suitable diluents for constitution of a lyophile. In certain embodiments, the pharmaceutically acceptable solvent further comprises a pharmaceutically acceptable acid.

Definitions

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

The term "pharmaceutically acceptable salt" refers to those salts which are, within the scope of sound medical judgment, suitable for use in contact with the tissues of humans and non-human animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, malonic acid, or methanesulfonic acid, or by using other methods known in the art such as ion exchange. Other pharmaceutically acceptable salts include adipate, alginate, ascorbate, aspartate, benzenesulfonate, benzoate, besylate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A solid formulation of Compound (1) described herein are characterized as "stable" if it undergoes less degradation than unformulated, solid, Compound (1), or a salt thereof, under the same conditions, including, e.g., time, temperature, and relative humidity (RH). A liquid formulation of Compound (1) described herein are characterized as "stable" if it undergoes less degradation than an unformulated liquid preparation (e.g., solution or suspension) of Compound (1), or a salt thereof, under the same conditions, including, e.g., time, temperature, and relative humidity.

EXAMPLES

Equipment and Materials

RUC-4 (Compound (1)) was supplied by CeleCor Therapeutics. All commercially available chemicals and materials were obtained from commercial vendors and used as received without further purification. Water suitable for HPLC analysis was Barnstead NanoPure or equivalent. Methanol was Fisher Optima® or equivalent. Isopropanol was Fisher HLPC Grade or equivalent. Acetonitrile was Fisher Optima® or equivalent. Trifluoroacetic acid (TFA) was Fisher Optima® or equivalent. HPLC analyses reported herein utilized an HPLC system capable of UV detection and equipped with a thermostatted column oven, thermostatted autosampler, and a quaternary or binary pump.

| | | | |
|---|---|---|---|
| HPLC column | Waters Atlantis T3 C18, 3 μm, 3.0 × 100 mm (Part # 186003722) | | |
| Wavelength | 238 nm | | |
| Flow rate | 0.6 mL/minute | | |
| Injection volume | 5 μL | | |
| Run time | 50 minutes, only acquire data for the first 35 minutes (Next injection delay 15 minutes) | | |
| | Peak | Retention time | RRT |
| Retention time | RUC-4 | ~12.8 minutes | ~1.00 |
| | Des-gly | ~11.7 minutes | ~0.91 |
| | Bis-gly | ~14.2 minutes | ~1.11 |
| | Acetamide | ~16.3 minutes | ~1.27 |
| Needle rinse | Diluent | | |
| Sample temperature | 25° C. | | |
| Column temperature | 55° C. | | |
| | Time (min) | Mobile Phase A (%) | Mobile Phase B (%) |
| Gradient parameters | 0.0 | 100 | 0 |
| | 0.5 | 100 | 0 |
| | 15.0 | 90 | 10 |
| | 25.0 | 50 | 50 |
| | 30.0 | 50 | 50 |
| | 35.0 | 100 | 0 |
| | 50.0 | 100 | 0 |

Example 1. Formulation Stability Tests

Formulation solutions as described in Table 3 below were prepared and divided in to three equal portions that were stored overnight (~18 hours) at −20° C., 5° C. and 20° C., respectively. The formulations were observed, and the characteristics reported in Table 3 were noted, immediately for RT, immediately upon removing 5° C. formulations from refrigerator, and upon thawing of −20° C. formulations. Clear solutions of Compound (1) were obtained at pH 4.75 at concentrations of ≤17.5 mg/mL. Physical instability at lower pH (4.75 to 5.00) is improved by formulating at lower drug concentrations (<17.5 mg/mL), thereby retaining chemical (e.g., low formation of Ds-Gly) and physical (e.g., low formation of crystals) stability characteristics.

TABLE 3

Formulations and Stabilities

| Formula | V1 | V2 | V3 | V4 | V5 | V7 | V8 | V10 | V11 | V12 |
|---|---|---|---|---|---|---|---|---|---|---|
| RUC-4, free base | 22 | 22 | 22 | 20 | 20 | 17.5 | 17.5 | 15 | 15 | 15 |
| Acetic acid, USP, 100% | 6.83 | 6.83 | 6.83 | 6.21 | 6.21 | 5.43 | 5.43 | 4.66 | 4.66 | 4.66 |
| Hydrochloric acid (1N) | 2.45 | 1.91 | 1.24 | 2.30 | 1.75 | 2.04 | 1.53 | 1.75 | 1.31 | 0.88 |
| Glycerin | 8.6 | 11.4 | 12.9 | 10.1 | 12.9 | 12.0 | 14.6 | 14.1 | 16.3 | 18.5 |
| Solution pH | 4.5 | 4.75 | 5.0 | 4.5 | 4.75 | 4.5 | 4.75 | 4.5 | 4.75 | 5.0 |
| Room Temp (20° C.) | G | G | G | G | G | G | G | G | G | G |
| Refrigerated (5° C.) | R | R | G | R | R | R | G | Y | G | G |
| Freeze-thaw (−20° C.) | R | R | G | R | R | R | G | Y | G | G |

Amounts listed in milligrams; All formulations with water QS to 1.0 mL

G: Clear solution results after overnight storage at RT, at 5° C., or after a freeze-thaw cycle.

Y: Mild haziness detected visually.

R: Hazy solution results after overnight storage at RT, at 5° C., or after a freeze-thaw cycle.

Example 2. Formulation Stability Tests

Formulation solutions as described in Table 4 were prepared and stored at −20° C., 5° C., and room temperature and were monitored for stability for extended periods of time (six months and in some cases longer). The formulations were observed for physical and chemical stability.

TABLE 4

Formulation Feasibility Study

| Formulation | S | U | V | W | X |
|---|---|---|---|---|---|
| RUC-4, free base | 22 mg | 22 mg | 22 mg | 22 mg | 22 mg |
| Glacial Acetic acid | 3.76 mg | 6.83 mg | 6.83 mg | 3.76 mg | 3.76 mg |
| Hydrochloric acid (1N) | qs to pH 5.0 ± 0.1 | qs to pH 5.0 ± 0.1 | qs to pH 5.0 ± 0.1 | qs to pH 5.0 ± 0.1 | qs to pH 5.0 ± 0.1 |
| Glycerin | — | — | 12.9 mg | 12.9 mg | 12.9 mg |
| Sodium Chloride | 4.1 mg | 4.1 mg | — | — | — |
| Sodium CMC, (250k Da, DS ~0.75) | — | — | — | — | 1.0 mg |
| Sterile Water for Injection | Qs to 1 mL | Qs to 1 mL | Qs to 1 mL | Qs to 1 mL | Qs to 1 mL |

TABLE 4-continued

| Formulation Feasibility Study | | | | | |
|---|---|---|---|---|---|
| Formulation | S | U | V | W | X |
| Change compared to Formula S | NA | Increased AcOH:RUC-4 ratio to 2 Retained NaCl | Increased AcOH:RUC-4 ratio to 2 Replaced NaCl with glycerin | Retained AcOH:RUC-4 ratio 1.1 Replaced NaCl with glycerin | Retained AcOH:RUC-4 ratio 1.1 Replaced NaCl with glycerin Included 0.1% of NaCMC |
| Solution pH | 4.98 | 5.04 | 5.01 | 4.98 | — |
| Chloride concentration | 138 mM | 102 mM | 34 mM | 71 mM | — |
| Stability observations | Solution clear at RT Haziness on refrigeration Precipitation on freezing | Solution clear at RT Haziness on refrigeration Precipitation on freezing Thawed solution hazy | Solution clear at RT No haziness or precipitation on cooling / freezing Thawing yields clear solution | Solution clear at RT Haziness on refrigeration Precipitation on freezing Tawed solution hazy, clarifies | — |

Example 3. Preparation of Lyophilized Formulation

The first step is to determine the amount of RUC-4 (at 100% purity), acetic acid, sucrose, and sterile WFI (water for injection) needed for the batch size. These calculations are based on preparation of 55 mg/mL RUC-4 concentration for the given batch size. A portion of the sterile WFI is weighed into a container with a mixer. The required amount of acetic acid is added next and the mixture is mixed for 5 minutes. Sucrose is added to the acetic acid solution and mixed to dissolve. RUC-4 is then added and mixed until it completely dissolves. The remaining amount of sterile WFI is added and the solution is mixed to complete the solution preparation process.

The final drug solution is filtered through a Millipak-20, 0.22-micron Durapore® membrane filter. After a successful filter integrity test, the filtered solution is aseptically filled into 5-mL clear-glass USP Type-1 vials (2.06 g+/−0.04 g fill per vial) to yield 110 mg of RUC-4 per vial.

Fill weight checks are done every 20 minutes. The vials are placed in trays and then loaded into a freeze-dryer. Freeze drying includes the following steps:

(i) Solutions are frozen on a shelf held at −45° C. for eight hours.
(ii) After the freezing and hold steps, the shelf is warmed to a temperature of −30° C. and ice sublimation (primary drying) is carried out at a chamber pressure of ~100 mTorr for 24 hours.
(iii) The shelf is then warmed to a temperature of −25° C. and ice sublimation (primary drying) is carried out at a chamber pressure of ~100 mTorr for another 24 hours.
(iv) At the end of primary drying, the shelf is heated to +25° C., and secondary drying is carried out at a chamber pressure of ~100 mTorr for 11 hours to remove absorbed water and achieve residual water content of ~1%.
(v) The chamber is purged with dry nitrogen.
(vi) Vials are stoppered and crimped.
(vii) Vials are stored at −5° C. until visual inspection is completed.
(viii) The finished product vials are stored at −20° C. until use.

Processing parameters described above may change depending upon the size of the batch and capacity of the lyophilizer. Also, storage conditions may also change depending upon the requirements.

The order of addition of excipients described above is critical as RUC-4 dissolves rapidly if it is added to the acetic acid solution. Following sterile filtration of RUC-4 solution, the physical integrity of the filter is tested to ensure its integrity was not compromised during filtration. This step is critical to ensuring the microbiological purity of the solution and final lyophilized product. The lyophilization process is robust as the primary and secondary temperatures chosen along with the duration of primary and secondary drying have been shown to be conservative based on the results from several development batches. Additionally, the lyophilization parameters chosen should ensure low moisture content in the finished product.

TABLE 5

| Quantitative Composition of the RUC-4 110 mg/vial Lyophilized Drug Product | | |
|---|---|---|
| Ingredient | Quantity (mg/vial) | Percentage (wt %) |
| Pre-lyophilization Solution | | |
| RUC-4 | 110 mg[1] | 5.34 |
| Acetic acid USP | 18.8 mg | 0.92 |
| Sucrose USP/NF | 47.2 mg | 2.29 |
| Sterile Water for Injection USP | qs to 2.06 g[2] | 91.45 |

NF = national formulary;
USP = United States Pharmacopeia;
qs = quantum satis, amount which is enough;
wt % = weight percentage
[1]Adjusted for purity of drug substance
[2]Removed during the drying process Embodiments 1. A composition comprising Compound (1):

(1)

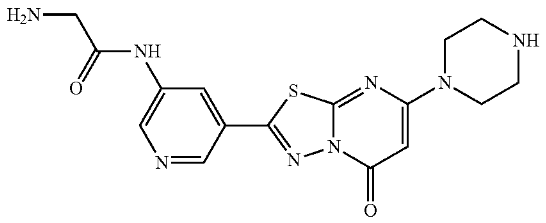

and acetic acid.

2. The composition of embodiment 1, wherein the molar ratio of Compound (1) to acetic acid is about 1:3.5.

3. The composition of any one of the preceding embodiments, wherein the composition is a solution in water having a pH of about 4.0-6.0, inclusive.

4. The composition of embodiment 3, wherein the pH is about 4.0-5.5, inclusive.

5. The composition of embodiment 3, wherein the pH is about 4.25-5.25, inclusive.

6. The composition of embodiment 3, wherein the pH is about 4.25-4.75, inclusive.

7. The composition of embodiment 3, wherein the pH is about 4.75-5.25, inclusive.

8. The composition of any one of embodiments 1-7, further comprising an additional acid or acids.

9. The composition of embodiment 8, wherein the additional acid or acids is one or more of a pharmaceutically acceptable organic acid and a pharmaceutically acceptable inorganic acid.

10. The composition of embodiment 9, wherein the pharmaceutically acceptable inorganic acid is hydrochloric acid.

11. The composition of embodiment 9, wherein the pharmaceutically acceptable organic acid is citric acid.

12. The composition of embodiment 10, wherein the total chloride ion concentration is ≤35 mM.

13. The composition of any one of the preceding embodiments, wherein the composition is a solution in water having an osmolality of ≥200 mmol/L.

14. The composition of any one of the preceding embodiments, comprising about 1-100 mg/mL of Compound (1).

15. The composition of embodiment 14, comprising about 5-25 mg/mL of Compound (1).

16. The composition of embodiment 14, comprising about 10-25 mg/mL of Compound (1).

17. The composition of embodiment 14, comprising about 10-20 mg/mL of Compound (1).

18. The composition of embodiment 14, comprising about 12-20 mg/mL of Compound (1).

19. The composition of embodiment 14, comprising about 15-20 mg/mL of Compound (1).

20. The composition of embodiment 14, comprising about 12-18 mg/mL of Compound (1).

21. The composition of embodiment 14, comprising about 15-18 mg/mL of Compound (1).

22. The composition of any one of the preceding embodiments, comprising about 3-15 mg/mL of acetic acid.

23. The composition of embodiment 22, comprising about 3-8 mg/mL of acetic acid.

24. The composition of embodiment 22, comprising about 3-7 mg/mL of acetic acid.

25. The composition of embodiment 22, comprising about 3-6 mg/mL of acetic acid.

26. The composition of embodiment 22, comprising about 4-8 mg/mL of acetic acid.

27. The composition of embodiment 22, comprising about 4-7 mg/mL of acetic acid.

28. The composition of embodiment 22, comprising about 4-6 mg/mL of acetic acid.

29. The composition of embodiment 22, comprising about 5-8 mg/mL of acetic acid.

30. The composition of embodiment 22, comprising about 5-7 mg/mL of acetic acid.

31. The composition of embodiment 22, comprising about 5-6 mg/mL of acetic acid.

32. The composition of embodiment 22, comprising about 10-15 mg/mL of acetic acid.

33. The composition of any one of the preceding embodiments, further comprising a polyol.

34. The composition of embodiment 33, wherein the polyol is glycerin (i.e., glycerol).

35. The composition of any one of embodiments 33-34, comprising about 1-50 mg/mL polyol.

36. The composition of embodiment 35, comprising about 10-30 mg/mL polyol.

37. The composition of embodiment 35, comprising about 10-20 mg/mL polyol.

38. The composition of embodiment 35, comprising 12-18 mg/mL polyol.

39. The composition of any one of the preceding embodiments, further comprising about 1-10 mg/mL citric acid.

40. The composition of embodiment 39, comprising about 3-8 mg/mL of citric acid.

41. The composition of embodiment 39, comprising about 5-8 mg/mL of citric acid.

42. The composition of embodiment 39, comprising about 3-5 mg/mL of citric acid.

43. The composition of embodiment 39, comprising about 0-3 mg/mL of citric acid.

44. The composition of embodiment 39, comprising about 1-3 mg/mL of citric acid.

45. The composition of embodiment 39, comprising about 1-2 mg/mL of citric acid.

46. The composition of embodiment 39, comprising about 2 mg/mL of citric acid.

47. The composition of embodiment 39, comprising about 1.35 mg/mL of citric acid.

48. The composition of embodiment 39, comprising about 1 mg/mL of citric acid.

49. The composition of any one of the preceding embodiments, further comprising Compound (2):

(2)

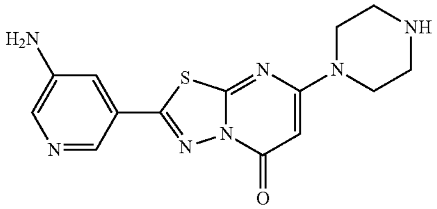

or a salt thereof.

50. The composition of embodiment 49, wherein Compound (2) or a salt thereof is present in an amount that is less than about 10% by weight, less than about 8% by weight, less than about 6% by weight, less than about 4% by weight, less than about 2% by weight, or less than about 1% by weight of the composition.

51. The composition of any one of the preceding embodiments, further comprising Compound (3):

(3)

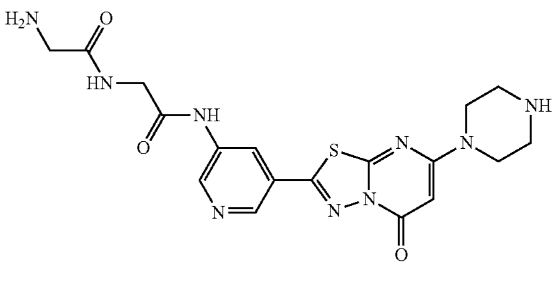

or a salt thereof.

52. The composition of embodiment 51, wherein Compound (3) is present in an amount that is less than about 10% by weight, less than about 8% by weight, less than about 6% by weight, less than about 4% by weight, less than about 2% by weight, or less than about 1% by weight of the composition.

53. The composition of embodiment 1, comprising the following components per milliliter of water:

| | |
|---|---|
| Compound (1) | 18 mg |
| Acetic acid | 5.59 mg |
| Hydrochloric acid | qs to pH 5.0 ± 0.1 |
| Glycerin | 14 mg |

wherein the composition has a pH of 5.0±0.1.

54. The composition of embodiment 1, comprising the following components per milliliter of water:

| | |
|---|---|
| Compound (1) | 17.5 mg |
| Acetic acid | 5.43 mg |
| Hydrochloric acid | 1.53 mg |
| Glycerin | 14.6 mg |

wherein the composition has a pH of 4.75±0.1.

55. The composition of embodiment 1, comprising the following components per milliliter of water:

| | |
|---|---|
| Compound (1) | 15 mg |
| Acetic acid | 4.66 mg |
| Hydrochloric acid | 1.31 mg |
| Glycerin | 16.3 mg |

wherein the composition has a pH of 4.75±0.1.

56. The composition of embodiment 1, comprising the following components per milliliter of water:

| | |
|---|---|
| Compound (1) | 15 mg |
| Acetic acid | 4.66 mg |
| Hydrochloric acid | 0.88 mg |
| Glycerin | 18.5 mg |

wherein the composition has a pH of 5.0±0.1.

57 The composition of embodiment 1, comprising the following components per milliliter of water:

| | |
|---|---|
| Compound (1) | 18 mg |
| Acetic acid | 5.6 mg |
| Anhydrous Citric Acid | 1.35 mg |
| Hydrochloric acid | 0.93 mg (QS pH to 4.75) |
| Glycerin | 16 mg |

wherein the composition has a pH of 4.75±0.1.

58. The composition of embodiment 1, comprising the following components per milliliter of water:

| | |
|---|---|
| Compound (1) | 18 mg |
| Acetic acid | 5.6 mg |
| Anhydrous Citric Acid | 1.35 mg |
| Hydrochloric acid | 1.4 mg (QS pH to 4.5) |
| Glycerin | 16.3 mg |

wherein the composition has a pH of 4.5±0.1.

59. The composition of embodiment 1, comprising the following components per milliliter of water:

| | |
|---|---|
| Compound (1) | 18 mg |
| Acetic acid | 5.6 mg |
| Anhydrous Citric Acid | 1.35 mg |
| Hydrochloric acid | 1.97 mg (QS pH to 4.25) |
| Glycerin | 18.5 mg |

wherein the composition has a pH of 4.25±0.1.

60. The composition of any one of the preceding embodiments, wherein the composition is stable for at least 1 month at 25° C./60% RH.

61. The composition of any one of the preceding embodiments, wherein the composition is stable for at least 3 months at 25° C./60% RH.

62. The composition of any one of the preceding embodiments, wherein the composition is stable for at least 6 months at 25° C./60% RH.

63. The composition of any one of the preceding embodiments, wherein the composition is stable for at least 12-18 months at 25° C./60% RH.

64. The composition of any one of the preceding embodiments, wherein the composition is stable for at least 1 year at 5° C.

65. The composition of any one of the preceding embodiments, wherein the composition is stable for at least 2 years at 5° C.

66. The composition of any one of the preceding embodiments, wherein the composition is stable for at least 3 years at 5° C.

67. The composition of any one of the preceding embodiments, wherein the composition is stable for at least 4 years at 5° C.

68. The composition of any one of the preceding embodiments, wherein the composition is stable for at least 5 years at 5° C.

69. A composition comprising Compound (1):

(1)

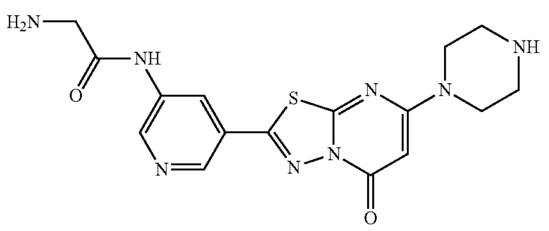

in the form of a salt of acetic acid.

70. The composition of embodiment 69, wherein the molar ratio of Compound (1) to acetic acid is in the range of about 1:0.5 to about 1:35.

71. The composition of embodiment 70, wherein the molar ratio of Compound (1) to acetic acid is about 1:1.

72. The composition of any one of embodiments 69-71, further comprising a sugar.

73. The composition of embodiment 72, wherein the sugar is a non-reducing sugar.

74. The composition of embodiment 73, wherein the non-reducing sugar is sucrose.

75. The composition of any one of embodiments 72-74, wherein the molar ratio of Compound (1) to the sugar is in the range of about 2:1 to about 1:2.

76. The composition of embodiment 75, wherein the molar ratio is in the range of about 2:1 to about 1:1.

77. The composition of embodiment 76, wherein the molar ratio is in the range of about 1.5:1 to about 1:1.

78. The composition of any one of embodiments 69-77, wherein the composition is a solution in water.

79. The composition of embodiment 78, wherein the solution is intended for lyophilization.

80. The composition of any one of embodiments 69-77, wherein the composition is a solid lyophile.

81. The composition of embodiment 80, comprising less than 5% by weight of Compound (4):

(4)

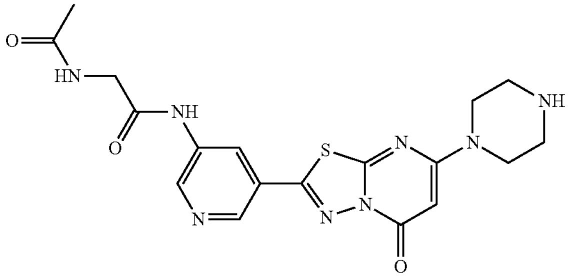

or a salt thereof.

82. The composition of embodiment 81, comprising less than about 4% by weight, less than about 3% by weight, less than about 2% by weight, less than about 1% by weight, or less than about 0.5% by weight of Compound (4).

83. The composition of any one of embodiments 80-82, wherein the composition is stable for at least 1 month at 25° C./60% RH.

84. The composition of any one of embodiments 80-82, wherein the composition is stable for at least 3 months at 25° C./60% RH.

85. The composition of any one of embodiments 80-82, wherein the composition is stable for at least 6 months at 25° C./60% RH.

86. The composition of any one of embodiments 80-82, wherein the composition is stable for at least 6-12 months at 25° C./60% RH.

87. The composition of any one of embodiments 80-82, wherein the composition is stable for at least 12-24 months at 25° C./60% RH.

88. The composition of any one of embodiments 80-82, wherein the composition is stable for at least 1 years at 5° C.

89. The composition of any one of embodiments 80-82, wherein the composition is stable for at least 2 years at 5° C.

90. The composition of any one of embodiments 80-82, wherein the composition is stable for at least 3 years at 5° C.

91. The composition of any one of embodiments 80-82, wherein the composition is stable for at least 4 years at 5° C.

92. The composition of any one of embodiments 80-82, wherein the composition is stable for at least 5 years at 5° C.

93. The composition of embodiment 78, wherein the solution is a reconstituted lyophile.

94. The composition of embodiment 93, comprising about 5-50 mg/mL of Compound (1).

95. The composition of embodiment 93, wherein the lyophile is a composition of any one of embodiments 33-43.

96. The composition of embodiment 93, further comprising sodium chloride.

97. A method of making a lyophilized composition of any one of embodiments 80-92, comprising:

providing a solution comprising Compound (1) and acetic acid;

filtering the solution;

freezing the solution; and removing the water from the frozen solution by sublimation at low pressure.

98. A method of making a solution of Compound (1) for administration by injection, comprising contacting Compound (1), or a pharmaceutically acceptable salt thereof, or a lyophile according to any one of embodiments 80-92 with a pharmaceutically acceptable solvent in a syringe.

99. The method of embodiment 98, wherein the syringe is a single chamber syringe.

100. The method of embodiment 98, wherein the syringe is a dual chamber syringe.

101. The method of embodiment 98, wherein the syringe is an autoinjector.

102. The method of any one of embodiments 98-101, wherein Compound (1), or the pharmaceutically acceptable salt thereof, or the lyophile, is present in the syringe prior to contact with the solvent.

103. The method of any one of embodiments 98-102, wherein the pharmaceutically acceptable solvent comprises water or saline.

104. The method of embodiment 103, wherein the pharmaceutically acceptable solvent further comprises a pharmaceutically acceptable acid.

The invention claimed is:

1. A composition comprising Compound (1):

(1)

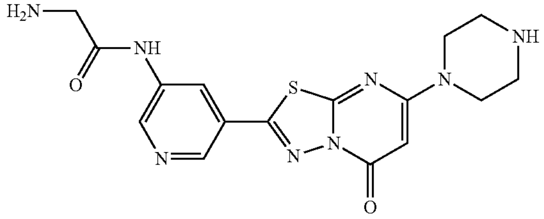

and acetic acid; wherein the composition is a solution in water having a pH of about 4.0-6.0, inclusive.

2. The composition of claim 1, wherein the molar ratio of Compound (1) to acetic acid is about 1:0.5 to about 1:3.5.

3. The composition of claim 1, further comprising an additional acid or acids.

4. The composition of claim 3, wherein the additional acid is hydrochloric acid.

5. The composition of claim 1, wherein the composition has an osmolality of ≥200 mmol/L.

6. The composition of claim 1, comprising about 1-100 mg/mL of Compound (1).

7. The composition of claim 1, comprising about 3-15 mg/mL of acetic acid.

8. The composition of claim 1, further comprising a polyol.

9. The composition of claim 1, further comprising about 1-10 mg/mL citric acid.

10. The composition of claim 1, further comprising Compound (2):

(2)

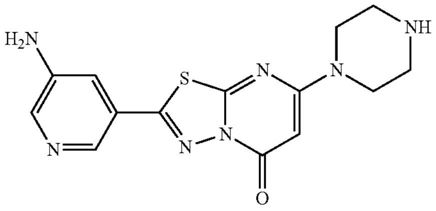

or a salt thereof.

11. The composition of claim 1, further comprising Compound (3):

(3)

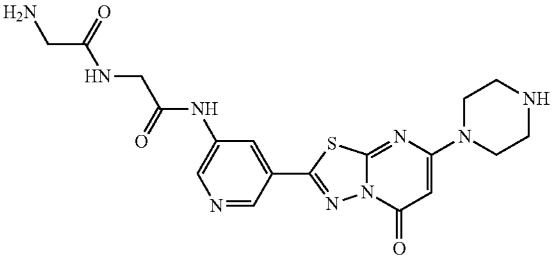

or a salt thereof.

12. The composition of claim 1, comprising the following components per milliliter of water:

| | |
|---|---|
| Compound (1) | 18 mg |
| Acetic acid | 5.59 mg |
| Hydrochloric acid | qs to pH 5.0 ± 0.1 |
| Glycerin | 14 mg |

wherein the composition has a pH of 5.0±0.1;

| | |
|---|---|
| Compound (1) | 17.5 mg |
| Acetic acid | 5.43 mg |
| Hydrochloric acid | 1.53 mg |
| Glycerin | 14.6 mg |

wherein the composition has a pH of 4.75±0.1;

| | |
|---|---|
| Compound (1) | 15 mg |
| Acetic acid | 4.66 mg |
| Hydrochloric acid | 1.31 mg |
| Glycerin | 16.3 mg |

wherein the composition has a pH of 4.75±0.1;

| | |
|---|---|
| Compound (1) | 15 mg |
| Acetic acid | 4.66 mg |
| Hydrochloric acid | 0.88 mg |
| Glycerin | 18.5 mg |

wherein the composition has a pH of 5.0±0.1;

| | |
|---|---|
| Compound (1) | 18 mg |
| Acetic acid | 5.6 mg |
| Anhydrous Citric Acid | 1.35 mg |
| Hydrochloric acid | 0.93 mg (QS pH to 4.75) |
| Glycerin | 16 mg |

wherein the composition has a pH of 4.75±0.1;

| | |
|---|---|
| Compound (1) | 18 mg |
| Acetic acid | 5.6 mg |
| Anhydrous Citric Acid | 1.35 mg |
| Hydrochloric acid | 1.4 mg (QS pH to 4.5) |
| Glycerin | 16.3 mg |

wherein the composition has a pH of 4.5±0.1; or

| | |
|---|---|
| Compound (1) | 18 mg |
| Acetic acid | 5.6 mg |
| Anhydrous Citric Acid | 1.35 mg |
| Hydrochloric acid | 1.97 mg (QS pH to 4.25) |
| Glycerin | 18.5 mg |

wherein the composition has a pH of 4.25±0.1.

13. The composition of claim 1, wherein the composition is stable for at least 1 month at 25° C./60% RH, at least 3 months at 25° C./60% RH, at least 6 months at 25° C./60% RH, or at least 12-18 months at 25° C./60% RH.

14. A composition comprising Compound (1):

(1)

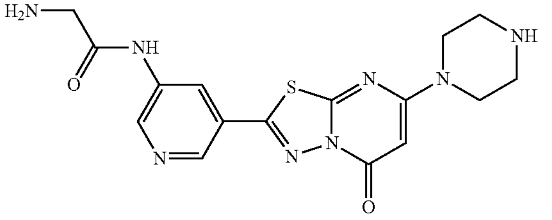

in the form of a salt of acetic acid, wherein the molar ratio of Compound (1) to acetic acid is in the range of about 1:0.2 to about 1:3.5.

15. The composition of claim 14, wherein the molar ratio of Compound (1) to acetic acid is in the range of about 1:0.5 to about 1:3.5.

16. The composition of claim 14, wherein the composition is a solid lyophile.

17. The composition of claim 16, comprising less than 5% by weight of Compound (4):

(4)

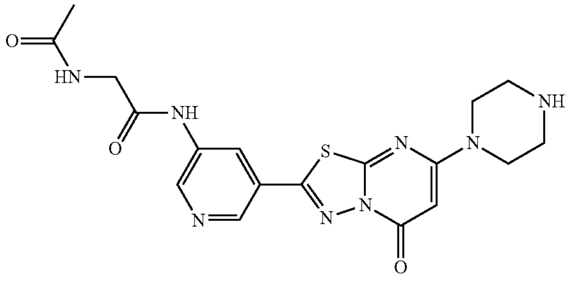

or a salt thereof.

18. A method of making a lyophilized composition of claim 16, comprising:

providing a solution comprising Compound (1) and acetic acid;

filtering the solution;

freezing the solution; and removing the water from the frozen solution by sublimation at low pressure.

19. A method of making a solution of Compound (1) for administration by injection, comprising contacting Compound (1), or a pharmaceutically acceptable salt thereof, or a lyophile according to claim 16 with a pharmaceutically acceptable solvent in a syringe.

20. The composition of claim 1, wherein the molar ratio of Compound (1) to acetic acid is about 1:0.5.

21. The composition of claim 1, wherein the composition comprises about 1 mg/mL to about 5 mg/mL acetic acid.

22. The composition of claim 8, wherein the composition comprises about 12-18 mg/mL polyol.

23. The composition of claim 1, comprising the following components per milliliter of water:

| | |
|---|---|
| Compound (1) | 18 mg |
| Acetic acid | 5.59 mg |
| Hydrochloric acid | qs to pH 5.0 ± 0.1 |
| Glycerin | 14 mg |

wherein the composition has a pH of 5.0±0.1.

* * * * *